(12) United States Patent
Morley et al.

(10) Patent No.: US 9,415,063 B2
(45) Date of Patent: Aug. 16, 2016

(54) TREATMENT OF NEUROLOGICAL DISORDERS

(71) Applicant: VELACOR THERAPEUTICS PTY LTD., Parkville, Vic (AU)

(72) Inventors: Grant Morley, Ascot Vale Vic (AU); Christopher Hovens, Surry Hills Vic (AU)

(73) Assignee: VELACOR THERAPEUTICS PTY LTD., Parkville (AU)

( * ) Notice: Subject to any disclaimer, the term of this patent is extended or adjusted under 35 U.S.C. 154(b) by 0 days.

(21) Appl. No.: 14/842,650

(22) Filed: Sep. 1, 2015

(65) Prior Publication Data

US 2015/0366902 A1    Dec. 24, 2015

Related U.S. Application Data

(63) Continuation of application No. 14/610,541, filed on Jan. 30, 2015, now abandoned, which is a continuation of application No. 12/681,569, filed as application No. PCT/AU2008/001470 on Oct. 3, 2008, now abandoned.

(60) Provisional application No. 60/977,281, filed on Oct. 3, 2007.

(51) Int. Cl.
*A61K 31/12* (2006.01)
*A61K 31/135* (2006.01)
(Continued)

(52) U.S. Cl.
CPC ............... *A61K 33/04* (2013.01); *A61K 31/12* (2013.01); *A61K 31/135* (2013.01); *A61K 31/137* (2013.01); *A61K 31/15* (2013.01);
(Continued)

(58) Field of Classification Search
CPC ..... A61K 8/23; A61K 33/04; A61K 2300/00; A61K 31/12; A61K 31/135; A61K 31/137; A61K 31/15; A61K 31/165; A61K 31/198; A61K 31/275; A61K 31/428; A61K 31/4453; A61K 31/46; A61K 31/473; A61K 31/48; A61K 31/4985; A61K 45/06
See application file for complete search history.

(56) References Cited

U.S. PATENT DOCUMENTS

| 4,810,497 A | 3/1989 | Horrobin |
| 5,925,349 A | 7/1999 | Rosen et al. |

(Continued)

FOREIGN PATENT DOCUMENTS

| AU | 5/227420 A1 | 5/2007 |
| EP | 0234733 B1 | 11/1991 |

(Continued)

OTHER PUBLICATIONS

TBI definition [online] retrieved on Apr. 11, 2016 from: http://emedicine.medscape.com/article/326510-overview; 4 pages.*

(Continued)

*Primary Examiner* — Ernst V Arnold
(74) *Attorney, Agent, or Firm* — Knobbe, Martens, Olson & Bear LLP (57) ABSTRACT

A treatment of a neurological disorder, including hypoxia, oxygen-glucose deprivation and acute brain trauma in a subject involves administering an effective amount of selenate or a pharmaceutically acceptable salt thereof to the subject. The treatment prevents incurring a symptom, holds in check a symptom or treats an existing symptom of the neurological disorder.

7 Claims, 5 Drawing Sheets

(51) Int. Cl.
| | |
|---|---|
| A61K 31/15 | (2006.01) |
| A61K 31/165 | (2006.01) |
| A61K 31/198 | (2006.01) |
| A61K 31/275 | (2006.01) |
| A61K 31/428 | (2006.01) |
| A61K 31/46 | (2006.01) |
| A61K 31/48 | (2006.01) |
| A61K 33/04 | (2006.01) |
| A61K 33/06 | (2006.01) |
| A61K 31/137 | (2006.01) |
| A61K 31/4453 | (2006.01) |
| A61K 31/473 | (2006.01) |
| A61K 31/4985 | (2006.01) |
| A61K 45/06 | (2006.01) |

(52) U.S. Cl.
CPC ............ *A61K 31/165* (2013.01); *A61K 31/198* (2013.01); *A61K 31/275* (2013.01); *A61K 31/428* (2013.01); *A61K 31/4453* (2013.01); *A61K 31/46* (2013.01); *A61K 31/473* (2013.01); *A61K 31/48* (2013.01); *A61K 31/4985* (2013.01); *A61K 45/06* (2013.01)

(56) References Cited

U.S. PATENT DOCUMENTS

| | | | |
|---|---|---|---|
| 6,123,956 A * | 9/2000 | Baker | A61K 9/0085 424/426 |
| 6,335,361 B1 * | 1/2002 | Hamilton | A61K 31/122 514/440 |
| 6,746,678 B1 | 6/2004 | Shapiro | |
| 2002/0061870 A1 | 5/2002 | Pearson et al. | |
| 2003/0175361 A1 | 9/2003 | Vaddadi | |
| 2004/0076758 A1 | 4/2004 | Lettmann et al. | |
| 2005/0142216 A1 | 6/2005 | Rindlesbach | |
| 2007/0026090 A1 | 2/2007 | Tirosh | |
| 2008/0004255 A1 | 1/2008 | Lyons | |

FOREIGN PATENT DOCUMENTS

| | | |
|---|---|---|
| EP | 1774972 A1 | 4/2007 |
| JP | 62185018 | 8/1987 |
| JP | H04-247033 A | 9/1992 |
| JP | H10-500939 A | 1/1998 |
| JP | 2005-525329 A | 8/2005 |
| JP | 2007-106732 | 4/2007 |
| JP | 2009-532340 A | 9/2009 |
| WO | 95/24920 | 9/1995 |
| WO | 03/066071 | 8/2003 |
| WO | 2004/016597 | 2/2004 |
| WO | 2004/099168 | 11/2004 |
| WO | 2005/017143 A1 | 2/2005 |
| WO | 2005/023247 A1 | 3/2005 |
| WO | 2007109851 | 10/2007 |
| WO | 2007109853 A1 | 10/2007 |

OTHER PUBLICATIONS

TBI definition [online] retrieved on Apr. 11, 2016 from: http://www.mayoclinic.org/diseases-conditions/traumatic-brain-injury/basics/definition/con-20029302?p=1; 14 pages.*
Calomme et al. (Selenium Deficiency Triggering Intractable Seizures in Therapeutic Uses of Trace elements 1996 Springer NY pp. 359-364).
Calbom (The Juice Lady's Guide to Juicing for Health, 1999, Penguin p. 150).
Schweizer et al. "Selenium and brain function: a poorly recognized liaison", Brain Research Reviews 2004 (45) 164-178.
Oztas, et al. "Influence of Antioxidants on the Blood-Brain Barrier Permeability During Epileptic Seizures" Journal of Neuroscience Research, 2001, vol. 66, pp. 674-678.
Gupta, et al. "Neuroprotective effect of antioxidants on ischaemia and reperfusion-induced cerebral injury", Pharmacological Research, 2003, vol. 43, pp. 209-215.
Santamaria et al, "Protective effects of the antioxidant selenium on quinolinic acid-induced neurotoxicity in rats: in vitro and in vivo studies", Journal Neurochemistry, 2003, vol. 86, pp. 479-488.
Belikov, Pharmaceutical Chemistry, M. Higher School, 1993, pp. 43-46.
Vaddadi, et al. "Low blood selenium concentrations in schizophrenic patients on clozapine", 2003 Blackwell Publishing Ltd. Br J Clin Pharmacol, 55, pp. 307-309.
Vinson et al. "Comparison of the Toxicity of Inorganic and Natural Selenium" Selenium in Biology and Medicine, edited by Combs, G.F., Levander, O.A., Spallholz, J.E. and Oldfield, J.E. Van Nostrand, NY, 1987 2 pages.
Zafar et al., "Dose-Dependent protective effect of selenium in rat model of Parkinson's disease: neurobehavioral and neurochemical evidences", Journal of Neurochemistry, 2003, 84, pp. 438-446.
Sajatovic et al. "Clozapine therapy in patients with neurological illness" Int. J. Psychiatry Med. 25:331 (1995).
Kern et al, "Massive cerebral embolization: successful treatment with retrograde perfusion", Ann Thorac Surg 2000, 69: pp. 1266-1268.
Bouma, et al., Cerebral circulation and metabolism after severe traumatic brain injury: the elusive role of ischemia, J. Neurosurg, 1991, vol. 75, pp. 685-693.
Davis, et al., The chemical forms of selenium influences 3,2'-Dimethyl-4-aminobiphenyl-DNA adduct formation in Rat colon, Biochemical and Molecular Roles of Nutrients, 1999, pp. 63-69.
Van Eersel, et al, Sodium selenate mitigates tau pathology, neurodegeneration, and functional deficits in Alzheimer's disease models, Proc. Nat'l. Acad. Sci. USA, 2010, vol. 107, Issue 31, pp. 13888-13893.
Feng, et al., Dietary Selenium Reduces the Formation of Aberrant Crypts in Rats Administered 3,2' -Dimethyl-4-aminobiphenyl, Toxicology and Applied Pharmacology, 1999, vol. 157, pp. 36-42.
Lu, et al., Dissociation of the Genotoxic and Growth Inhibitory Effects of Selenium, Biochemical Pharmacology, 1995, vol. 50, Issue 2, pp. 213-219.
Mayo clinic, Alzheimer's disease, [online] retrieved from http://www.mayoclinic.com/health/alzheimers-disease/DS00161/METHOD=print (cited in the Office Action dated Feb. 4, 2011 in U.S. Appl. No. 12/295,270).
Mayo clinic, Parkinson's disease, [online] retrieved from http://www.mayoclinic.com/healthlparkinsons-disease/DS00295/METHOD=print (cited in the Office Action dated Feb. 4, 2011 in U.S. Appl. No. 12/295,270).
Menter, et al., Selenium Effects on Prostate Cell Growth, Cancer Epidemiol Biomarkers & Prevention, 2000, vol. 9, pp. 1171-1182.
Stewart, et al., Selenium Compounds Have Disparate Abilities to Impose Oxidative Stress and Induce Apoptosis, Free Radical Biology & Medicine, 1999, vol. 26, pp. 42-48.
Cho, et al., Brain Slices as Models for Neurodegenerative Disease and Screening Platforms to Identify Novel Therapeutics, Current Neuropharmacology, 2007, vol. 5, pp. 19-33.
Finley, et al., Selenium (Se) from high-selenium broccoli is utilized differently than selenite, selenate and selenomethionine, but is more effective in inhibiting colon carcinogenesis, BioFactors, 2001, vol. 14, pp. 191-196.
Zwillich, Panel: No evidence of Alzheimer's prevention., [online] retrieved from http://www.webmd.com/alzheimers/news/20100428/panel-no-evidence-alzheimers-prevention (cited in the Office Action dated Feb. 4, 2011 in U.S. Appl. No. 12/295,270).
Mayo Clinic Schizophrenia Jan. 30, 2010 (online) retrieved from: http://www.mayoclinic.com/health/schizophrenia/DS00196/METHOD=print&DSECTION=all on Jan. 19, 2011; 8 pages.
Mayo Clinic Huntington's Disease May 8, 2009 (online) retrieved from: http://www.mayoclinic.com/health/huntingtons-disease/DS00401/METHOD=print&DSECTION=all on Jan. 19, 2011; 8 pages.
Mayo Clinic Anxiety Jun. 29, 2010 (online) retrieved from: http://www.mayoclinic.com/health/anxiety/DS01187/METHOD= print on Jan. 19, 2011; 9 pages.

(56) References Cited

OTHER PUBLICATIONS

Mayo Clinic Depression Feb. 11, 2010 (online) retrieved from: http://www.mayoclinic.com/health/depression/DS00175/METHOD-print on Jan. 19, 2011; 14 pages.
Mayo Clinic Creutzfeldt-Jakob May 14, 2010 (online) retrieved from: http://www.mayoclinic.com/helth/depression/DS00175/METHOD= print on Jan. 19, 2011; 7 pages.
Mayo Clinic Epilepsy (online) retrieved from http://www.mayoclinic.com/health/epilepsy/DS00342/METHOD=print&DSECTION=all on Jan. 20, 2011; Apr. 28, 2009; 10 pages.
Corcoran et al. (Journal of Clinical Neuroscience 2010, 17 pp. 1025-1033).
Klevay (Pharmacology & Therapeutics. Art A: chemotherapy, Toxicology and Metabolic inhibitors 1967, 1(2), 211-222).
Ramaekers et al. Neuropediatric 1994, 25(4), 217-223).
Weber et al. (Lancet 1991, 337: 1443-44)).
Alzheimer's [online] retrieved on May 5, 2013 from: http://www.mayoclinic.com/health/alzheimers-disease/DS00161; Jan. 19, 2013; 15 pages.
Dementia [online] retrieved on May 5, 2013 from: http:/www.mayoclinic.com/health/dementia/DS01131; Apr. 16, 2013; 17 pages.
Alzheimer's [online] retrieved on May 5, 2013 from: http://www.cdc.gov/features/alzheimers/; Jun. 4, 2010; 4 pages.
What Causes Parkinson's Disease? [online] retrieved on May 6, 2013 from: http://www.webmd.com/parkinsons-disease/guide/parkinsons-causes; Aug. 13, 2012; 3 pages.
Lei et al, "Tau protein: Relevance to Parkinson's disease," The International Journal of Biochemistry & Cell Biology 2010, 42, 1775-1778.
Kasuya, "Effect of Selenium on the Toxicity of Methylmercury on Nervous Tissue in Culture", Toxicology and Applied Pharmacology, 1976, 35, pp. 11-20.
Delacourte, "Tauopathies: recent insights into old diseases", Folia Neuropathologica, 2005, 43(4):244-257.
Mayo clinic alzheimer's; [online] retrieved from http://www.mayoclinic.com/health/alzheimers-disease/DS00161/METHOD=print on Jan. 29, 2011; 12 pages.
Mayo clinic alzheimer's; [online] retrieved from http://ww.mayoclinic/health/parkinsons-disease/DS00295 on Jan. 29, 2011; 9 pages.
Foster, et al. "Frontotemporal Dementia and Parkinsonism Linked to Chromosome 17: A consensus Conference," American Neurological Association, 1997, 41:706-715.
Alzheimer's disease, Mayoclinic [online] retrieved from: http://www.mayoclinic.org/diseases-conditions/alzheimers-disease/basics/definition/con-20023871; Jan. 19, 2013; 15 pages.
Always, et al. "Stroke Essentials for Primary Care: A Practical Guide 2009", 3 pages.
Ehmann, et al. "Brain trace elements in Pick's Disease," Abstract of: Ann Neurol. 1984. 15(1):102-4), 1 page.
Sodium selenite [online] retrieved from http://www/sigmaaldrich.com/catalog/product/sial/s0882?lang=en&region=US# on Nov. 14, 2015; 3 pages.
Anderson et al., Abnormally phosphorylated tau is associated with neuronal and axonal loss in experimental autoimmune encephalomyelitis and multiple sclerosis, Brain, 2008; 131:1736-1748.
Kuhlmann et al., "Acute axonal damage in multiple sclerosis is most extensive in early disease stages and decreases over time," Brian (2002), 125, 2202-2212.
"What is a Stroke?—The Stroke Foundation", www.thestrokefoundation.com/index.php/about-stroke/27-what-is-a-stroke, retrieved on Feb. 23, 2015. 1 page.

\* cited by examiner

TREATMENT OF NEUROLOGICAL DISORDERS

FIELD OF THE INVENTION

This invention relates to the use of selenate or a pharmaceutically acceptable salt thereof in methods and compositions of treating or preventing non-tauopathy neurological disorders. In some embodiments, the invention relates to the use of selenate or a pharmaceutically acceptable salt thereof in combination with other therapies for use in methods of treating or preventing non-tauopathy neurological disorders.

BACKGROUND OF THE INVENTION

Neurological disorders are disorders that affect the central nervous system, the peripheral nervous system or the autonomic nervous system.

There has recently been some evidence presented in the literature that tau protein is not only implicated in neurodegenerative disorders such as Alzheimer's disease, but also in other neurological disorders, [Satch et al., 2006; Wen et al., 2004; Roberson et al., 2007; Deutsch et al., 2006; Bartosik-Psujek, 2006, Ost et al., 2006].

One type of abnormal tau protein is hyperphosphorylated tau protein. Tau protein is known to be phosphorylated at a number of phosphorylation sites by glycogen synthase kinase 3β (GSK3β) in vivo, including the Alzheimer's disease specific Ser$^{396}$ residue [Li and Paudel, 2006]. In turn, GSK3β is known to be phosphorylated by the protein kinase Akt and the activity of Akt is known to be attenuated by the protein phosphatase PP2A.

It has recently been shown that PP2A accounts for approximately 71% of the total tau phosphatase activity of human brain [Liu et al., 2005]. The total phosphatase activity and the activities of PP2A toward tau are significantly decreased in brains of Alzheimer's disease patients whereas that of other phosphatases such as PP2B are actually increased in the Alzheimer's disease brain [Liu et al., 2005]. PP2A activity negatively correlates to the level of tau phosphorylation at most phosphorylation sites in human brains. This indicates that PP2A is the major tau phosphatase that regulates its phosphorylation at multiple sites in human brain. This implies that the abnormal hyperphosphorylation of tau is partially due to a downregulation of PP2A activity in the Alzheimer's disease brain and that agents that can act to boost the activity of PP2A would have clinical utility in treating and/or preventing development of some neurological disorders.

There is a need for agents that reduce the amount of tau protein or affect the phosphorylation of tau protein and are clinically useful in the treatment or prevention of neurological disorders.

SUMMARY OF THE INVENTION

The present invention is based, at least in part, on the implication of tau protein, such as hyperphosphorylated tau protein, in a number of non-tauopathy neurological diseases and that the activity of the protein phosphatase PP2A may be enhanced by exposure to selenate or a pharmaceutically acceptable salt thereof. The enhancement of the activity of PP2A may reduce or inhibit phosphorylation of tau protein, especially hyperphosphorylation, with a two pronged approach: i) dephosphorylation and inactivation of Akt, thereby reducing phosphorylation of GSK3β and consequently reducing phosphorylation of tau protein, and ii) direct dephosphorylation of tau protein. A reduction in the phosphorylation, including hyperphosphorylation of tau protein reduces or prevents the accumulation or deposition of abnormal tau protein in neurons and glial cells and therefore is useful in the treatment or prevention of neurological disorders.

Accordingly, in one aspect, the present invention provides a method for the treatment or prevention of a non-tauopathy neurological disorder in a subject comprising administering to the subject an effective amount of selenate or a pharmaceutically acceptable salt thereof and wherein the non-tauopathy neurological disorder is not an α-synucleopathy. In some embodiments the non-tauopathy neurological disorder is selected from the group consisting of Creutzfeldt-Jakob disease, Huntington's disease, stroke, cerebral ischaemia, dementia associated with stroke or cerebral ischaemia, dementia associated with HIV, disorders associated with excitotoxicity, epilepsy, seizures, schizophrenia, multiple sclerosis, acute brain trauma (severe traumatic brain injury) and oxygen glucose deprivation.

In another aspect of the invention, there is provided a use of selenate or a pharmaceutically acceptable salt thereof in the manufacture of a medicament for treating or preventing a non-tauopathy neurological disorder, wherein the non-tauopathy neurological disorder is not an α-synucleopathy.

In some embodiments of the methods and uses broadly described above, the selenate or a pharmaceutically acceptable salt thereof is administered in combination with other therapies suitable for treatment or prevention of non-tauopathy neurological disorders or therapies suitable for relieving the symptoms of non-tauopathy neurological disorders.

In another aspect of the invention there is provided a method of reducing the amount of tau protein in a cell comprising exposing the cell to an effective amount of selenate or a pharmaceutically acceptable salt thereof.

DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size or amount that varies by as much as 30%, 20% or 10% to a reference quantity, level, value, dimension, size or amount.

Throughout the specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The term "dephosphorylation" as used herein, refers to the chemical removal of a phosphate group ($PO_4^{2-}$) from a biochemical entity such as a protein. Under cellular conditions, dephosphorylation is achieved enzymatically by an enzyme such as a phosphatase.

The term "hyperphosphorylation" refers to the circumstance where phosphorylation sites on a biochemical entity such as a protein, are phosphorylated at a level higher than normal. The phrase "inhibiting or reducing hyperphosphorylation" includes preventing all sites or some sites on a biochemical entity from being phosphorylated and decreasing the number of biochemical entities that have all or some of their phosphorylation sites phosphorylated.

As used herein, the term "in combination with" refers to the treatment of a subject with at least two agents such that their effects on the neurological disorder occur, at least in part, over the same time period. Administration of at least two agents may occur simultaneously in a single composition, or each agent may be simultaneously or sequentially administered in separate compositions.

The term "non-tauopathy neurological disorder" as used herein refers to a neurological disorder which does not display the pathology of classical tauopathies. In general tauopathies are considered to be a group of diverse dementias and movement disorders which have as a common pathological feature, the presence of intracellular aggregations of abnormal filaments of tau protein. The tau protein in the aggregations may be hyperphosphorylated tau. These aggregations of tau protein filaments in tauopathies can be identified by standard diagnostic techniques such as staining and light microscopy. In contrast, non-tauopathy neurological disorders, some of which while associated with aberrant tau protein, such as hyperphosphorylated tau protein, or to an abnormal amount of tau protein, do not display intracellular aggregations of abnormal tau. Examples of non-tauopathy neurological disorders include Creutzfeldt-Jakob disease, Huntington's disease, stroke, cerebral ischaemia, dementia associated with stroke or cerebral ischaemia, dementia associated with HIV, disorders associated with excitotoxicity, epilepsy, seizures, schizophrenia, multiple sclerosis, acute brain trauma (severe traumatic brain injury) and oxygen glucose deprivation.

As used herein the term "α-synucleopathy" refers to a neurodegenerative disorder or disorder that involves aggregation of α-synuclein or abnormal α-synuclein in nerve cells in the brain. The non-tauopathy neurological disorders of the present invention are not α-synucleopathies.

As used herein, the term "disorders associated with excitotoxicity'" are disorders that involve excessive activation of glutamate receptors in the brain. Disorders associated with excitotoxicity include, ischaemia during stroke, trauma, hypoxia, hypoglycaemia and hepatic encephalopathy; disorders related to long term plastic changes in the central nervous system such as chronic pain, drug tolerance, drug dependence, drug addiction and tardive dyskinesia, epilepsy, schizophrenia, anxiety, depression, acute pain and tinnitis.

As used herein, the term "nutritional amount" includes an amount of selenium that is less than the maximum FDA restricted dietary supplement dose. In the United States, the maximum daily dose for a dietary supplement is 400 μg per day.

By "pharmaceutically salt" as used herein in relation to selenate, means salts which are toxicologically safe for human and animal administration. For example, suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, iron, nickel, zinc, ammonium and alkylammonium.

Basic nitrogen-containing groups may be quarternised with such agents as lower alkyl halide, such as methyl, ethyl, propyl and butyl chlorides, bromides and iodides; dialkyl sulfates like dimethyl and diethyl sulfate; and others.

Suitable metal ion salts of selenate include, but are not limited to, sodium, potassium, lithium, magnesium, calcium, iron, nickel, zinc, ammonium and alkylammonium salts. A preferred salt of selenate is the sodium salt, $Na_2SeO_4$.

The term "phosphorylation" as used herein refers to the chemical addition of a phosphate group ($PO_4^{2-}$) to a biochemical entity such as a protein. Under cellular conditions phosphorylation is achieved enzymatically by an enzyme such as a kinase. The phrase "inhibiting or reducing phosphorylation" includes preventing phosphorylation of one or more phosphorylation sites on a biochemical entity, including preventing phosphorylation of all phosphorylation sites as in hyperphosphorylation. This phrase also includes decreasing the extent of phosphorylation of a biochemical entity by preventing phosphorylation occurring at one or more phosphorylation sites or as a result of dephosphorylation occurring at one or more phosphorylated sites on the biochemical entity.

The terms "subject" or "individual" or "patient", used interchangeably herein, refer to any subject, particularly a vertebrate subject and more particularly a mammalian subject, for whom prophylaxis or treatment is desired. Suitable vertebrate animals that fall within the scope of the invention include, but are not limited to, primates, avians, livestock animals (e.g. pigs, sheep, cows, horses, donkeys), laboratory test animals (e.g. rabbits, mice, rats, guinea pigs, hamsters), companion animals (e.g. cats and dogs) and captive wild animals (e.g. foxes, deer, dingoes). A preferred subject is a human in need of treatment or prophylaxis of a neurological disorder. However, it will be understood that the aforementioned terms do not imply that symptoms are present.

The term "supranutritional" as used herein, refers to an amount which is greater than the amount considered as a nutritional requirement. In the United States, the FDA defined maximum daily dose for selenium dietary supplementation is 400 μg per day. A supranutritional amount of selenium provides selenium to a subject above the maximum daily dose for dietary supplementation. For example, a supranutritional amount of selenium per day may be 5 μg/kg to 1.0 mg/kg, 5 μg/kg to 0.5 mg/kg per day, 5 μg/kg to 0.3 mg/kg, 0.01 mg/kg to 1.0 mg/kg, 0.01 mg/kg to 0.5 mg/kg, 0.025 mg/kg to 1.0 mg/kg, 0.025 mg/kg to 0.5 mg/kg, 0.05 mg/kg to 1.0 mg/kg, 0.05 mg/kg to 0.5 mg/kg, 0.05 mg/kg to 0.3 mg/kg, 0.1 mg/kg to 1.0 mg/kg, 0.1 mg/kg to 0.5 mg/kg or 0.1 mg/kg to 0.3 mg/kg, especially 0.025 mg/kg to 0.3 mg/kg or 0.01 mg/kg to 0.3 mg/kg per day.

As used herein, the term "effective amount" in the context of treating or preventing a neurodegenerative disease or inhibiting or reducing phosphorylation of tau protein or inhibiting the activity of GSK3β is meant the administration or addition of an amount of selenate or a pharmaceutically acceptable salt thereof, either in a single dose or as part of a series of doses, that is effective in enhancing the activity of PP2A and especially that is effective for the prevention of incurring a symptom, holding in check such symptoms, and/or treating existing symptoms, associated with the neurological disorder. The effective amount will vary depending on the health and physical condition of the individual to be treated, the taxonomic group of the individual to be treated, the formulation of the composition, the assessment of the medical situations and other relevant factors. It is expected that the amount will fall within a relatively broad range. In specific embodiments, an effective amount is a nutritional or supranutritional amount.

2. Methods of Treating or Preventing Non-Tauopathy Neurological Disorders

The present invention is predicated in part on the determination that selenate or a pharmaceutically acceptable salt thereof, is effective in enhancing the activity of PP2A which in turn may result in a reduction in phosphorylation of tau protein by GSK3β and/or an increase in the rate of dephosphorylation of tau protein. It has also been observed that selenate or a pharmaceutically acceptable salt thereof is effective in decreasing the level or amount of tau protein present in cells.

The present invention can be used effectively to treat or prevent non-tauopathy neurological disorders. Suitably, the effective amount of selenate or a pharmaceutically acceptable salt thereof is a nutritional or supranutritional amount of selenate. In some embodiments, the amount of selenate or a pharmaceutically acceptable salt thereof delivers a supranutritional dose of selenium in an amount of from about 5 µg/kg to about 1.0 mg/kg, usually from about 0.01 mg/kg to 1.0 mg/kg or 0.01 mg/kg to 0.5 mg/kg per day or 0.01 mg/kg to 0.3 mg/kg per day. In preferred embodiments, the selenate or a pharmaceutically acceptable salt thereof is sodium selenate ($Na_2SeO_4$).

In some embodiments, the selenate or a pharmaceutically acceptable salt thereof is administered to a subject in combination with another therapy for treating or preventing a non-tauopathy neurological disorder. Illustrative examples of therapies for treating or preventing a non-tauopathy neurological disorder that may be used in combination with selenate or a pharmaceutically acceptable salt thereof include, but are not limited to, antiplatelet agents such as aspirin (e.g., 50-325 mg/day), clopidogrel (e.g., 75 mg/day), aspirin and dipyridamole (e.g., 25/200 mg twice daily) and ticlopidine, antihypertensive agents, antidepressants, anti-convulsant drugs such as carbamazepine (Tegretol™), clobazam (Frisium™), clonazepam (Klonopin™), ethosuximide (Zarontin™), felbamate (Felbatol™), fosphenytoin (Cerebyx™), flurazepam (Dalmane™), gabapentin (Neurontin™), lamotrigine (Lanictal™), levetiracetam (Keppra™), oxcarbazepine (Trileptal™), mephenytoin (Mesantoin™), phenobarbital (Luminal™), phenytoin (Dilantin™), pregabalin (Lyrica™), primidone (Mysoline™), sodium valproate (Epilim™), tiagabine (Gabitril™), topiramate (Topamax™), valproate semisodium (Depakote™, Epival™), valproic acid (Depakene™, Convulex™), vigabatrin (Sabril™), diazepam (Valium™), lorazepam (Ativan™), paraldehyde (Paral™) and pentobarbital (Nembutal™); anti-psychotic drugs including typical anti-psychotic drugs such as phenothiazines including chlorpromazine (Thorazine™), fluphenazine (Prolixin™), perphenazine (Trilafon™), prochlorperazine (Compazine™), thioridazine (Mellaril™), trifluoperazine (Stelazine™), mesoridazine, promazine, triflupromazine (Vesprin™) and levomepromazine (Nozinan™); thioxanthenes such as chlorprothixene, flupenthixol (Depixol™ and Fluanxol™), thiothixene (Navane™) and zuclopenthixol (Clopixol™ and Acuphase™) and butyrophenones such as haloperidol (Haldol™), droperidol, pimozide (Orap™) and melperone; atypical anti-psychotic drugs including clozapine (Clozaril™), olanzapine (Zyprexa™), risperidone (Risperdal™), quetiapine (Seroquel™), ziprasidone (Geodon™), amisulpride (Solian™) and paliperidone (Invega™); dopamine partial agonists such as aripiprazole (Abilify™), bifeprunox and norclozapine (ACP-104), interferons such as interferon β-1a (Aronex™, Rebif™, CinnoVex™) and interferon β-1b (Betaseron™); glatiramer acetate (Copaxone™); mitoxantrone (Novantrone™); natalizumab (Tysabri™) and riluzole (Rilutek™).

Combination therapies could include effective amounts of selenate or a pharmaceutically acceptable salt thereof together with an agent used for treating or preventing a non-tauopathy neurological disorder in an amount normally used in the absence of selenate. Alternatively the amount of agent used in the treatment of non-tauopathy neurological disorders may be decreased upon co-administration with selenate or a pharmaceutically acceptable salt thereof. In some embodiments, the combination may display a synergistic effect.

Certain embodiments of the present invention are directed to methods for treating or preventing non-tauopathy neurological disorders in a subject, which methods generally comprise administering to the subject an effective amount of selenate or a pharmaceutically acceptable salt thereof. To practice these methods, the person managing the subject can determine the effective dosage form of selenate or a pharmaceutically acceptable salt thereof for the particular condition and circumstances of the subject. An effective amount of selenate is one that is effective for the treatment or prevention of a non-tauopathy neurological disorder, including prevention of incurring a symptom, holding in check a symptom and treating a symptom. In some embodiments, the effective amount is a nutritional amount. In other embodiments, the effective amount is a supranutritional amount. In specific embodiments, the selenate or a pharmaceutically acceptable salt thereof is sodium selenate.

Modes of administration, amounts of selenate administered, and selenate formulations, for use in the methods of the present invention, are discussed below. The non-tauopathy neurological disorder to be treated may be determined by measuring one or more diagnostic parameters indicative of the course of the disease, compared to a suitable control. In the case of a human subject, a "suitable control" may be the individual before treatment, or may be a human (e.g., an age-matched or similar control) treated with a placebo. In accordance with the present invention, the treatment of non-tauopathy neurological disorders includes and encompasses without limitation: (i) preventing a non-tauopathy neurological disorder in a subject who may be predisposed to the disease but has not yet been diagnosed with the disease and, accordingly, the treatment constitutes prophylactic treatment for the non-tauopathy neurological disorder; (ii) inhibiting a non-tauopathy neurological disorder, i.e., arresting the development of the non-tauopathy neurological disorder; or (iii) relieving symptoms resulting from the non-tauopathy neurological disorder.

The methods of the present invention are suitable for treating an individual who has been diagnosed with a non-tauopathy neurological disorder, who is suspected of having a non-tauopathy neurological disorder, or who is known to be susceptible and who is considered likely to develop a non-tauopathy neurological disorder.

In particular embodiments, the selenate is sodium selenate.

Exemplary subjects for treatment with the methods of the invention are vertebrates, especially mammals. In certain embodiments, the subject is selected from the group consisting of humans, sheep, cattle, horses, bovine, pigs, dogs and cats. A preferred subject is a human.

The selenate or a pharmaceutically acceptable salt thereof may be formulated by following any number of techniques known in the art of drug delivery. Selenate or a pharmaceutically acceptable salt thereof may of course be administered by a number of means keeping in mind that all formulations are not suitable for every route of administration. Selenate or a pharmaceutically acceptable salt thereof can be administered in solid or liquid form. The application may be oral, rectal, nasal, topical (including buccal and sublingual), or by inhalation. Selenate or a pharmaceutically acceptable salt thereof may be administered together with conventional pharmaceutical acceptable adjuvant, carriers and/or diluents.

The solid forms of application comprise tablets, capsules, powders, pills, pastilles, suppositories and granular forms of administration. They may also include carriers or additives, such as flavors, dyes, diluents, softeners, binders, preservatives, lasting agents and/or enclosing materials. Liquid forms of administration include solutions, suspensions and emulsions. These may also be offered together with the above-mentioned additives.

Solutions and suspensions of selenate or a pharmaceutically acceptable salt thereof, assuming a suitable viscosity for ease of use, may be injected. Suspensions too viscous for injection may be implanted using devices designed for such purposes, if necessary. Sustained release forms are generally administered via parenteral or enteric means. Parenteral administration is another route of administration of the selenate or a pharmaceutically acceptable salt thereof used to practice the invention. "Parenteral" includes formulations suitable for injection and for nasal, vaginal, rectal, and buccal administration.

The administration of selenate or a pharmaceutically acceptable salt thereof may involve an oral dose formulation. Oral dose formulations are preferably administered once daily to three times daily in the form of a capsule or tablet, or alternatively as an aqueous based solution. Selenate or a pharmaceutically acceptable salt thereof may be administered intravenously either daily, continuously, once a week or three times a week.

The administration of selenate or a pharmaceutically acceptable salt thereof may include daily administration, preferably once daily in the form of a sustained release capsule or tablet, or once daily as an aqueous solution.

Combinations of selenate or a pharmaceutically acceptable salt thereof and at least one agent that is suitable, for treating a neurological disorder and may be administered in solid or liquid form in a single formulation or composition or in separate formulations or compositions. In some embodiments, the selenate or a pharmaceutically acceptable salt thereof and the agent for treating a neurological disorder are administered orally as a single tablet or capsule or separate tablets or capsules. In other embodiments, the selenate or a pharmaceutically acceptable salt thereof and the agent for treating a neurological disorder are administered intravenously in a single composition or separate compositions.

The present invention also provides pharmaceutical compositions for treating or preventing a neurological disorder, comprising a nutritional or supranutritional amount of selenate or a pharmaceutically acceptable salt thereof. In some embodiments, the compositions contain an amount of selenate that delivers selenium in an amount of from about 40 µg to about 80 mg, for example, 400 µg to 80 mg, of selenium as part of selenate or a pharmaceutically acceptable salt thereof, and a pharmaceutically acceptable carrier. In some embodiments, the selenate or its pharmaceutically acceptable salt delivers selenium in an amount of about 40 µg to about 80 mg or 400 µg to 80 mg. In illustrative examples, the selenate or a pharmaceutically acceptable salt thereof delivers selenium in an amount of about 400 µg to 80 mg, 401 µg to 80 mg, 500 µg to 40 mg, especially 800 µg to 40 mg, for a single or divided daily dose.

The pharmaceutical compositions comprising selenate or a pharmaceutically acceptable salt thereof may further comprise another agent for treating or preventing a neurological disorder. For example, the composition may contain selenate or a pharmaceutically acceptable salt thereof and at least one antiplatelet agent such as aspirin (e.g., 50-325 mg/day), clopidogrel (e.g., 75 mg/day), aspirin and dipyridamole (e.g., 25/200 mg twice daily) and ticlopidine, antihypertensive agents, antidepressants, anti-convulsant drugs such as carbamazepine (Tegretol™), clobazam (Frisium™), clonazepam (Klonopin™), ethosuximide (Zarontin™), felbamate (Felbatol™), fosphenytoin (Cerebyx™), flurazepam (Dalmane™), gabapentin (Neurontin™), lamotrigine (Lanictal™), levetiracetam (Keppra™), oxcarbazepine (Trileptal™), mephenytoin (Mesantoin™), phenobarbital (Luminal™), phenytoin (Dilantin™), pregabalin (Lyrica™), primidone (Mysoline™), sodium valproate (Epilim™), tiagabine (Gabitril™), topiramate (Topamax™), valproate semisodium (Depakote™, Epival™), valproic acid (Depakene™, Convulex™), vigabatrin (Sabril™), diazepam (Valium™), lorazepam (Ativan™), paraldehyde (Paral™) and pentobarbital (Nembutal™); anti-psychotic drugs including typical anti-psychotic drugs such as phenothiazines including chlorpromazine (Thorazine™), fluphenazine (Prolixin™), perphenazine (Trilafon™), prochlorperazine (Compazine™), thioridazine (Mellaril™), trifluoperazine (Stelazine™), mesoridazine, promazine, triflupromazine (Vesprin™) and levomepromazine (Nozinan™); thioxanthenes such as chlorprothixene, flupenthixol (Depixol™ and Fluanxol™), thiothixene (Navane™) and zuclopenthixol (Clopixol™ and Acuphase™) and butyrophenones such as haloperidol (Haldol™), droperidol, pimozide (Orap™) and melperone; atypical anti-psychotic drugs including clozapine (Clozaril™), olanzapine (Zyprexa™), risperidone (Risperdal™), quetiapine (Seroquel™), ziprasidone (Geodon™), amisulpride (Solian™) and paliperidone (Invega™); dopamine partial agonists such as aripiprazole (Abilify™), bifeprunox and norclozapine (ACP-104), interferons such as interferon β-1a (Aronex™, Rebif™, CinnoVex™) and interferon β-1b (Betaseron™); glatiramer acetate (Copaxone™); mitoxantrone (Novantrone™); natalizumab (Tysabri™) and riluzole (Rilutek™).

The pharmaceutical composition of the present invention may include any additional components that are non-immunogenic and biocompatible with selenate, as well as capable of bioabsorption, biodegradation, elimination as an intact molecule. The formulation may be supplied in a ready-to-use form or may be supplied as a sterile powder or liquid requiring vehicle addition prior to administration. If sterility is desired, the formulation may be made under sterile conditions, the individual components of the mixture may be sterile, or the formulation may be sterile filtered prior to use. Such a solution can also contain appropriate pharmaceutically acceptable carriers, such as but not limited to buffers, salts, excipients, preservatives, etc.

In some embodiments, oral formulations are used for administering selenate or a pharmaceutically acceptable salt thereof in the methods of the invention. These formulations generally comprise selenate or a pharmaceutically acceptable salt thereof having decreased solubility in order to delay absorption into the bloodstream. In addition, these formulations may include other components, agents, carriers, etc., which may also serve to delay absorption of the selenate or a pharmaceutically acceptable salt thereof. Microencapsulation, polymeric entrapment systems, and osmotic pumps, which may or may not be bioerodible, may also be used to allow delayed or controlled diffusion of the selenate or a pharmaceutically acceptable salt thereof from a capsule or matrix.

The selenate or a pharmaceutically acceptable salt thereof can be used solus or as part of another agent. Accordingly, the present invention also contemplates an agent that comprises selenate or a pharmaceutically acceptable salt thereof for the treatment of a neurological disorder.

In another aspect of the invention there is provided a method of reducing the amount of tau protein in a cell comprising exposing the cell to an effective amount of selenate or a pharmaceutically acceptable salt thereof.

In some embodiments of this aspect, the tau protein is abnormally phosphorylated such as hyperphosphorylated.

In other embodiments, the tau protein has a normal amount of phosphorylation.

While not wishing to be bound by theory, tau protein appears to be implicated in neurological disease and appears to be a mediator of neurotoxic insults. Reduction of the amount of tau protein, with normal levels of phosphorylation or hyperphosphorylation, may be neuroprotective.

In order that the nature of the present invention may be more clearly understood and put into practical effect, particular preferred embodiments thereof will now be described with reference to the following non-limited examples.

EXAMPLES

Example 1

Investigation into the neuroprotective effects of sodium selenate, sodium selenite and selenomethionine, against excitotoxicity, hypoxia and ischaemia in cultured rat hippocampal slices.

Methods:

Organotypic hippocampal slice cultures were prepared using the basic method of Pringle et al 1997, modified as follows:

Wistar rat pups (8-11 days old) were decapitated and the hippocampus rapidly dissected into ice-cold Gey's balanced salt solution supplemented with 4.5 mg/mL glucose. Transverse sections (400 µm) were cut on a McIlwain tissue chopper and placed back into ice-cold Gey's balanced salt solution. Slices were separated and plated onto Millicell CM culture inserts (4 per well) and maintained at 37° C./5% $CO_2$ for 14 days. Maintenance medium consists of 25% heat-inactivated horse serum, 25% Hank's balanced salt solution (HBSS) and 50% minimum essential medium with added Earle's salts (MEM), supplemented with 1 mM glutamine and 4.5 mg/mL glucose. Medium was changed every 3-4 days.

Hypoxia:

Experimental hypoxia was performed previously (Pringle et al., 1996; 1997). Briefly, 14 day cultures were transferred to serum free medium (SFM—75% MEM, 25% HBSS supplemented with 1 mM glutamine and 4.5 mg/mL glucose) containing 5 µg/mL of the fluorescent exclusion dye propidium iodide (PI). Cultures were allowed to equilibrate in SFM for 60 minutes prior to imaging. PI fluorescence was detected using a Leica DMIL inverted microscope fitted with a rhodamine filter set. Any cultures in which PI fluorescence is detected at this stage was excluded from further study. Hypoxia was induced by transferring cultures to serum free media (SFM) (+PI) which had been saturated with 95% $N_2$/5% $CO_2$. Culture plates (without lids) were sealed into an airtight chamber in which the atmosphere was saturated with 95% $N_2$/5% $CO_2$ by continuously blowing through gas at 10 L/min for ten minutes before being sealed and placed in the incubator for 170 minutes (total time of hypoxia was therefore 180 minutes). At the end of the hypoxic period cultures were returned to normoxic SFM containing PI and placed back in the incubator for 24 hours. Mn(III)tetrakis(4-benzoic acid)porphyrin chloride (MnTBAP) at 100 µM was used as a positive neuroprotective control. The efficacy of the compounds under investigation was assessed using a pre, during and post-hypoxia paradigm—compounds being present in the medium 24 hours pre-hypoxia, during the 3 hours of hypoxia and 24 hours post-hypoxia.

Ischaemia:

Experimental ischaemia was induced by transferring cultures to glucose deficient media (GFM-75% MEM, 25% HBSS supplemented with 1 mM glutamine)+PI, which had been saturated with 95% $N_2$/5% $CO_2$. Culture plates (without lids) were then sealed into an airtight chamber in which the atmosphere was saturated with 95% $N_2$/5% $CO_2$ by continuously blowing through gas at 10 L/min for ten minutes before being sealed and placed in the incubator for 50 minutes (total time of ischaemia was therefore 60 minutes). At the end of the ischaemic period cultures were returned to normoxic SFM containing PI and placed back in the incubator for 24 hours. MnTBAP at 100 µM was used as a positive neuroprotective control. The efficacy of the compounds under investigation was assessed using a pre, during and post-hypoxia paradigm—compounds being present in the medium 24 hours pre-ischaemia, during the 1 hour of ischaemia and 24 hours post-ischaemia.

Determination of Neuronal Damage

Neuronal damage was assessed using ImageJ software running on a PC. Images being captured using a monochrome CCD camera and saved for offline analysis. Light transmission images were captured prior to the addition of drugs, and PI fluorescence images recorded at the end of the 24-hour recovery period. The area of the CA1 region was then determined from the transmission image. The area of PI fluorescence in the CA1 is measured using the threshold function on ImageJ, and neuronal damage expressed as the percentage of the CA1 in which PI fluorescence is detected above background (Pringle et al., 1997).

Compounds

The experimental compounds tested were all obtained from Sigma Aldrich

Sodium selenate (cat.# S8295)
Sodium selenite (cat.#00163)
Selenomethionine (cat.# S3132)

Figure 1:
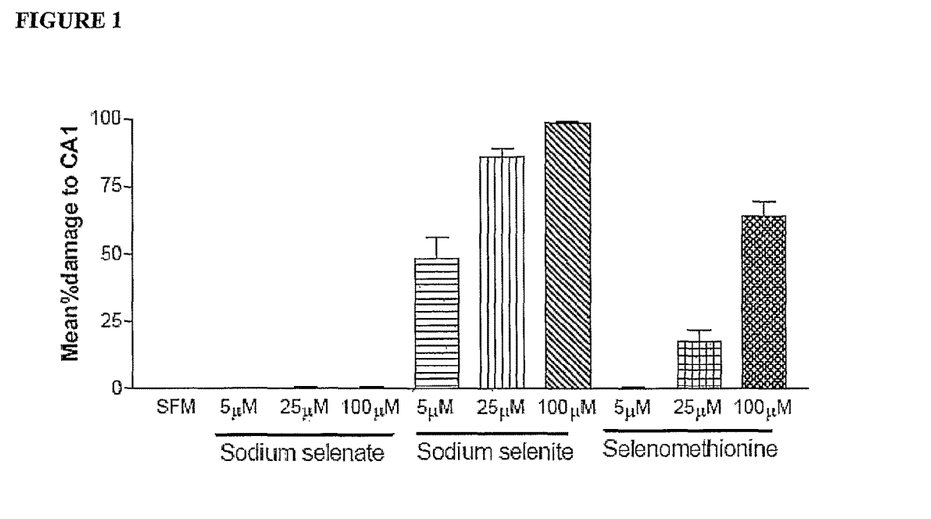
FIG. 1 is a graphical representation showing the tissue culture toxicity of sodium selenate, sodium selenite and selenomethionine in serum free media at 5 µM, 25 µM and 100 µM after 24 hours exposure.
Figure 2:
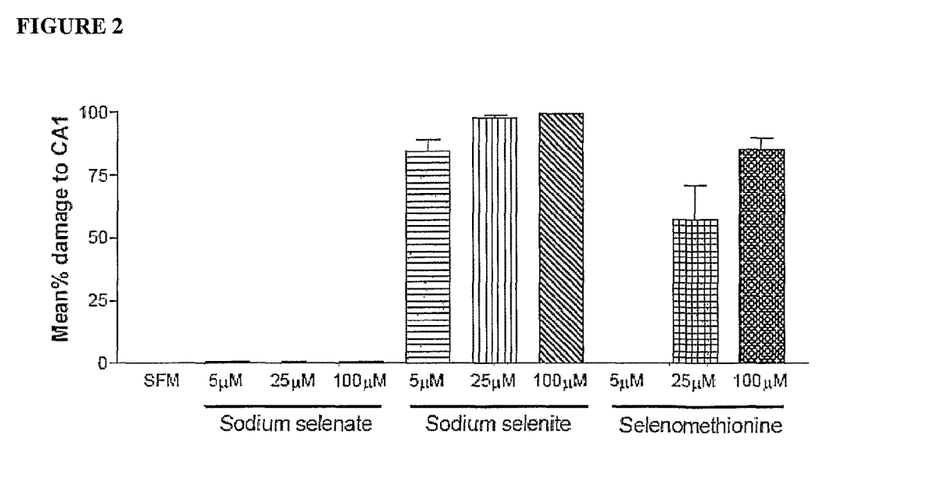
FIG. 2 is a graphical representation showing the tissue culture toxicity of sodium selenate, sodium selenite and selenomethionine in serum free media at 5 µM, 25 µM and 100 µM after 48 hours exposure.

A preliminary toxicity screen was carried out on the compounds to determine tissue culture exposure levels that would cause toxicity. Each compound was made to 5 mM in SFM, then used at 1 µL/mL, 5 µK/mL and 20 µL/mL, to give final concentrations of 5 µM, 25 µM and 100 µM. Damage was measured after 24 hours and 48 hours. (Results shown in FIGS. 1 and 2). Sodium selenite was found to be toxic above 5 µM and selenomethionine was toxic above 25 µM. Sodium selenate was not found to be toxic at any concentration tested up to 100 µM. These results were used to determine the concentrations used in subsequent experiments.

The compounds were made to 10 mM in SFM. Sodium selenate was serially diluted with SFM to 1 mM, 100 µM and 5 µM, each of these was used at 10 µL/mL, to give final concentrations of 50 nm, 1 µM, 10 µM and 100 µM. Sodium selenite was diluted to 100 µM, selenomethionine to 500 µM. These were then used at 10 µL/mL to give final concentrations of 1 µM and 5 µM.

In view of the results obtained from the hypoxia experiment, (Results FIG. 3), the concentrations of sodium selenate used in the OGD experiment were increased.

In this case the sodium selenate was made to 50 mM in SFM, then serially diluted to 25 mM, 10 mM and 1 mM, each of these used at 10 µL/mL to give final concentrations of 10 µM, 100 µM, 250 µM and 500 µM. Sodium selenite and selenomethionine as before. An experiment to assess the toxicity of sodium selenate at these higher concentrations was run in parallel with the OGD (Results FIG. 4).

Results

Figure 3:
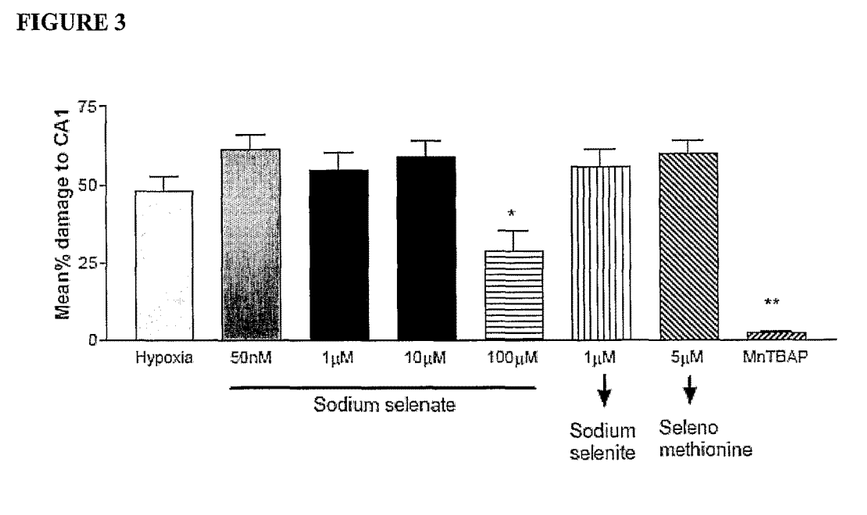
FIG. 3 is a bar chart graphical representation illustrating the effects of sodium selenate, sodium selenite and selenomethionine on hypoxia induced neurodegeneration compared with the neuroprotectant MnTBAP.

In cultures exposed to hypoxia alone, PI fluorescence was observed 48%±4.4% of the CA1 region (n=48), and this was prevented by 100 µM MnTBAP (n=24, P<0.01 vs hypoxia alone). Significant attenuation of damage was also seen with 100 µM sodium selenate (P<0.05 vs hypoxia alone, n=24) but not with the other test compounds. FIG. 3.

Figure 4:
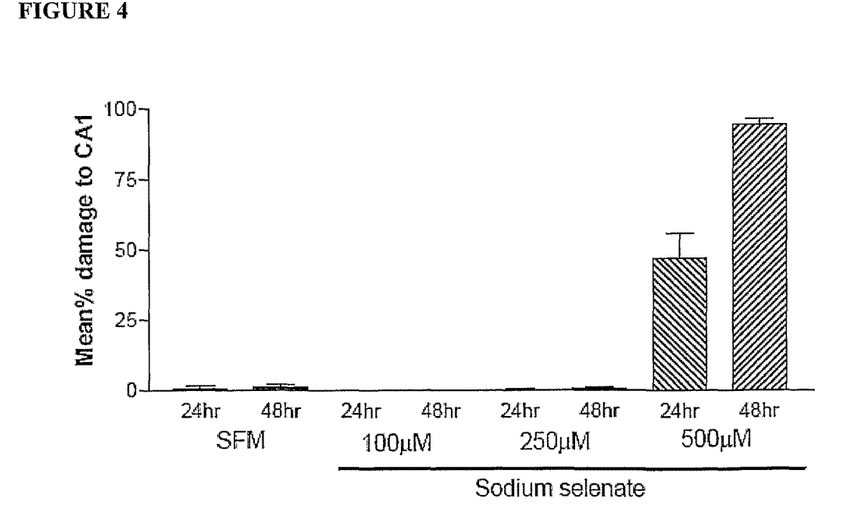
FIG. 4 is a bar chart graphical representation illustrating the toxicity of sodium selenate in tissue culture at 100 µM, 250 µM and 500 µM.
Figure 5:
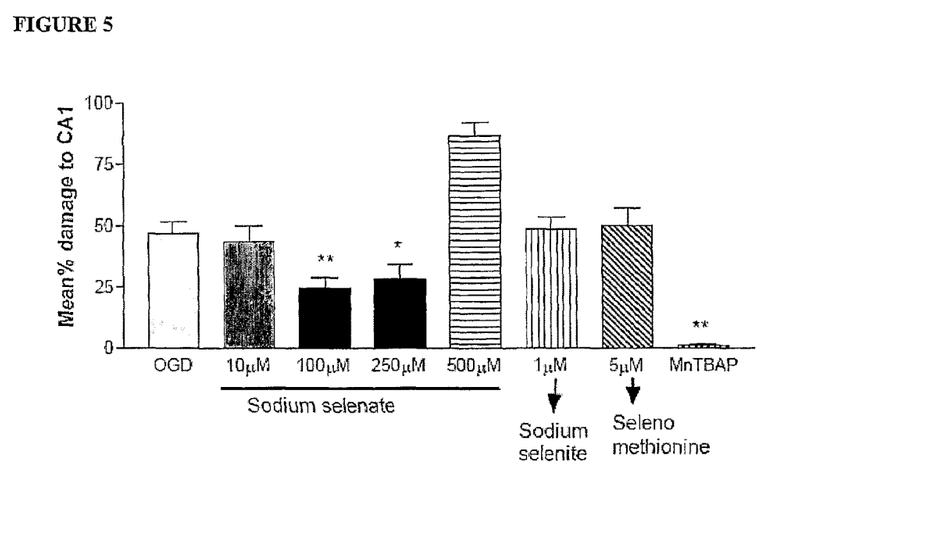
FIG. 5 is a bar chart representation showing the effects of sodium selenate, sodium selenite and selenomethionine on ischaemia induced neurodegeneration.

In cultures exposed to oxygen glucose deprivation (OGD) ischaemia alone, PI fluorescence was observed in 47% 4.5% of the CA1 region (n=48), and this was prevented by 100 µM MnTBAP (n=24, P<0.01 vs OGD alone). Significant attenuation of damage was seen with 100 µM sodium selenate (P<0.01 vs OGD alone, n=24), and with 250 µM sodium selenate (P<0.05 vs OGD alone, n=24) but not with the other test compounds (see FIG. 5). There was a significant increase in toxicity seen with 500 µM sodium selenate after hypoxia but which was subsequently shown to be due to neurotoxicity of the compound at this concentration in the absence of hypoxia (FIG. 4).

Example 2

PTZ Induced Seizure Activity in Rats

Materials and Methods
Animals

All animal experiments were carried out according to the National Institute of Health (NIH) guidelines for the care and use of laboratory animals, and approved by the Ethical Committee of the National Laboratory Animal Center, Kuopio, Finland. Altogether 30 adult male Sprague-Dawley rats (Taconic, Denmark) weighing 200-240 g were used. Animals were housed at a standard temperature (22±1° C.) and in a light-controlled environment (lights on from 7 am to 8 pm) with ad libitum access to food and water.

Animals were grouped as follows:
10 rats treated with vehicle (sterile water as drinking water).
10 rats treated with sodium selenate anhydrous (120 microgram in 100 mL sterile water), p.o in drinking water for 7 days prior to PTZ injection.
10 rats treated with sodium selenate anhydrous (1.2 milligram in 100 mL sterile water), p.o in drinking water for 7 days prior to PTZ injection.

PTZ Induced Seizures

Pentylenetetrazol (PTZ) (60 mg/kg) is administered intraperitoneally (i.p., 2 mL/kg in saline) to male Sprague-Dawley rats.

Drug Delivery

Sodium selenate is administered p.o in drinking water for 7 days prior to PTZ injection. The rats have ad libitum access to water (normal daily consumption of water is 30 mL/rat/day).

Monitoring of Seizure Activity

Behavioural changes were observed for 30 minutes following PTZ administration. The incidence of seizures (seizure and severe seizure), the latency for the first seizure appearance and the duration of seizure activity were used as indices of anticonvulsant effect. Seizure numbers were not counted if the animal died. Mortality typically was the result of one very severe seizure which was recorded as a single severe seizure. Animals that died were assigned the maximum seizure duration of 30 minutes. In one instant an animal (no. 1) had only one very intense and prolonged seizure, in this case only 1 single severe seizure was recorded. Severe seizure was defined as a prolonged seizure involving stretching and twisting convulsions.

Statistical Analysis

Values are presented as percentages and differences are considered to be statistically significant at the P<0.05 level. Statistical analysis was performed using StatsDirect software. Differences among groups were analyzed by 1-way-ANOVA followed by Dunnet's test (comparison to the control (=vehicle treated PTZ rats) group).

Results
Mortality

Mortality was observed in the vehicle group (1 animal) and the 120 µg sodium selenate group (1 animal).

Number of Seizures

Figure 6:
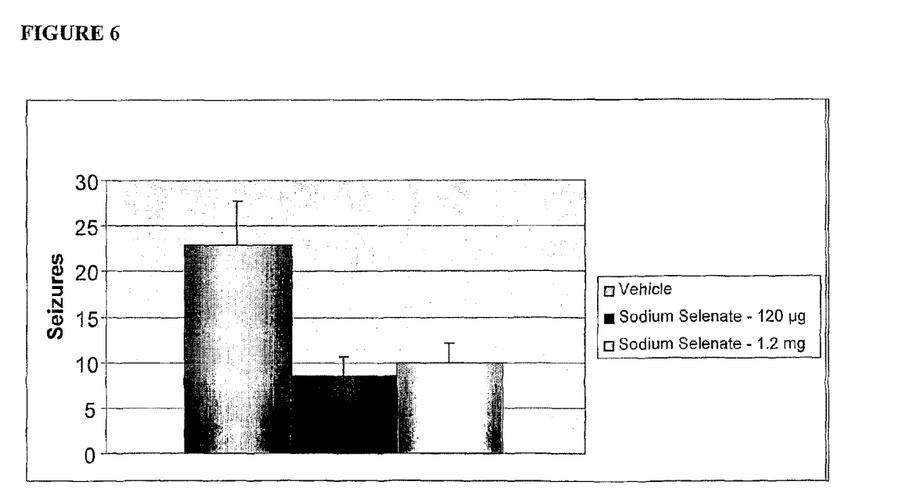
FIG. 6 is a graphical representation illustrating the number of PTZ induced seizures in rats exposed to 120 µg and 1.2 mg of sodium selenate (mean±SEM).

Animals receiving vehicle experienced 22.8±4.9 seizures. Sodium selenate significantly reduced the number of seizures to 8.5±2.1 in the 120 µg group and 9.9±2.2 in the 1.2 mg group (FIG. 6).

Number of Severe Seizures

Figure 7:
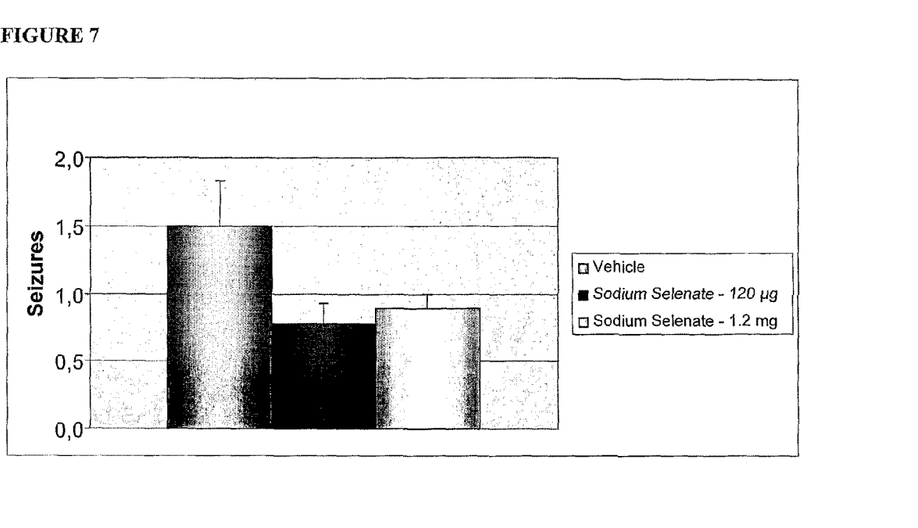
FIG. 7 is a graphical representation illustrating the number of PTZ induced severe seizures in rats exposed to 120 µg and 1.2 mg of sodium selenate (mean ±SEM).

Animals receiving vehicle experienced 1.5±0.3 severe seizures. Sodium selenate significantly reduced the number of seizures to 0.8±0.1 in the 120 µg group. Animals treated with 1.2 mg sodium selenate experienced 0.9±0.1 severe seizures (FIG. 7).

Duration of Seizure Activity

Figure 8:
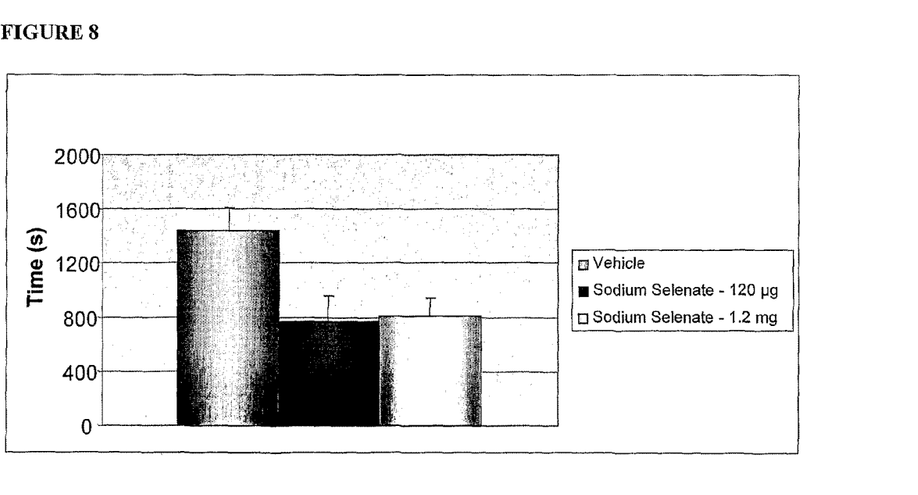
FIG. 8 is a graphical representation illustrating the duration of seizure activity in rats injected with PTZ exposed to 120 µg and 1.2 mg of sodium selenate (mean ±SEM).

The duration of seizure activity of animals receiving vehicle was 1443.4±166.3 seconds. Sodium selenate treatment significantly reduced duration of seizure activity at both 120 µg (770.9±189.9 secs) and 1.2 mg (808.6±126.1 secs) (FIG. 8).

Latency to Seizure Onset

Figure 9:
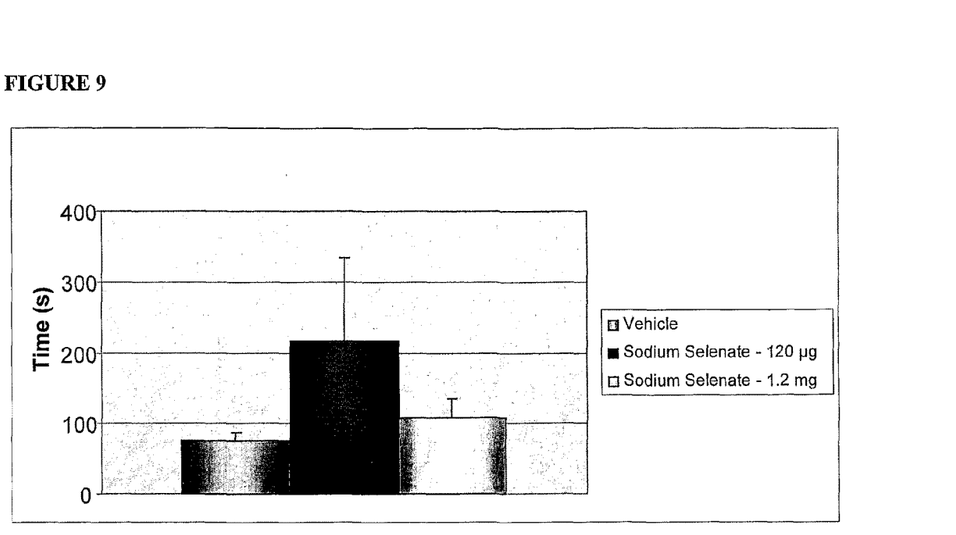
FIG. 9 is a graphical representation illustrating the latency to seizure onset in rats injected with PTZ exposed to 120 µg and 1.2 mg of sodium selenate (mean±SEM).

Animals receiving vehicle experienced seizure onset at 76.4±10.7 seconds. Animals receiving sodium selenate at 120 µg and 1.2 mg experienced seizure onset at 217.6±117.6 seconds and 107.6±26.9 seconds respectively. There were no significant differences in seizure onset between groups (FIG. 9).

CONCLUSIONS

These data demonstrate that sodium selenate reduces the number of seizures and duration of seizure activity at both 120 µg and 1.2 mg in response to PTZ administration. Sodium selenate at 120 µg also reduced the number of severe seizures experienced following PTZ administration. Neither dose of compound had a significant effect on the latency to seizure onset in this model.

REFERENCES

Bartosik-Psujek, H. and Stelmasiak, Z., *The CSF levels of total-tau and phosphotau in patients with relapsing-remitting multiple sclerosis*. J. Neural. Transm. 2006. March; 113(3):339-45.

Deutsch, S. I., Rosse, R. B. and Lakshman, R. M., *Dysregulation of tau phosphorylation is a hypothesized point of convergence in the pathogenesis of alzheimer's disease, frontoemporal dementia and schizophrenia with therapeutic implications*. Progress in neuro-psychopharmacology & biological psychiatry. 2006. vol. 30, 8:1369-1380.

Li, T. and Paudel, H. K., *Glycogen Synthase Kinase 3β phosphorylates Alzheimer's disease-specific Ser 396 of microtubule-associated protein tau by a sequential mechanism*. Biochemistry, 2006, 45(10): p.3125-3133.

Liu, F., et al., *Contributions of protein phophatases PP1, PP2A, PP2B and PP5 to the regulation of tau phosphorylation*. Eur. J. Neurosci. 2005. 22(8): p. 1942-50.

Ost, M., Nylén, K., Csajbok, L., Ohrfelt, A. O., Tullberg, M., Wikkelsö, C., Nellgård, P., Rosengren, L., Blennow, K. and Nellgård, B., *Initial CSF total tau correlates with 1-year outcome in patients with traumatic brain injury*. Neurology. 2006. Nov. 14; 67(9):16004.

Pringle, A. K., Benham, C. D., Sim, L., Kennedy, J., Iannotti, F., Sundstrom, L. E., *Selective N-type calcium channel agonist omega conotoxin MVIIA is neuroprotective against hypoxic neurodegeneration in organotypic hippocampal slice cultures*. Stroke. 1996. November; 27(10:2124-30.

Pringle, A. K., Angunawela, R., Wilde, G. J., Mepham, J. A., Sundstrom, L. E., Iannotti, F., *Induction of 72 kDa heat-shock protein following sub-lethal oxygen deprivation in organotypic hippocampal slice cultures*. Neuropathal. Appl. Neurobiol. 1997. August 23(4):289-98.

Roberson, E. D., Scearce-Levie, K., Palop, J. J., Yan, F., Cheng, I. H., Wu, T., Gerstein, H., Yu, G. Q. and Mucke, L., *Reducing endogenous tau ameliorates amyloid beta-induced deficits in an Alzheimer's disease mouse model*. Science, 2007, 316, 750.

Satoh, K., Shirabe, S., Eguchi, H., Tsujino, A., Eguchi, K., Satoh, A., Tsujihata, M., Niwa, M., Katamine. S., Kurihara, S. and Matsuo, H., *14-3-3 protein, total tau and phosphorylated tau in cerebrospinal fluid of patients with Creutzfeldt-Jakob disease and neurodegenerative disease in Japan*. Cell Mol. Neurobiol. 2006. February; 26(1):45-52.

Wen, Y., Yang, S., Liu, R. and Simpkins, J. W., *Transient cerebral ischemia induces site-specific hyperphosphorylation of tau protein*. Brain Res. 2004. October 1; 1022(1-2): 30-8.

What is claimed is:

1. A method for the treatment of traumatic brain injury in a subject comprising administering an effective amount of selenate or a pharmaceutically acceptable salt thereof, wherein the treatment prevents incurring a symptom, holds in check a symptom or treats an existing symptom of said traumatic brain injury.

2. The method according to claim 1 wherein the effective amount of selenate or a pharmaceutically acceptable salt thereof delivers a supranutritional amount of selenium.

3. The method according to claim 2 wherein the supranutritional amount of selenium is 5 µg/kg to 1.0 mg/kg per day.

4. The method according to claim 1 wherein the selenate is in the form of sodium selenate.

5. The method according to claim 2 wherein the supranutritional amount of selenium is 0.05 mg/kg to 1 mg/kg per day.

6. The method of claim 1 wherein the amount of selenate or a pharmaceutically acceptable salt thereof which is administered is sufficient to enhance the activity of PP2A in the subject.

7. The method of claim 1 wherein the traumatic brain injury is a result of physical trauma to the brain.

* * * * *